United States Patent [19]

Czarnik et al.

[11] Patent Number: 4,780,536

[45] Date of Patent: Oct. 25, 1988

[54] HEXAAZATRIPHENYLENE HEXANITRILE AND ITS DERIVATIVES AND THEIR PREPARATIONS

[75] Inventors: Anthony W. Czarnik; Kuppusamy Kanakarajan, both of Columbus, Ohio

[73] Assignee: The Ohio State University Research Foundation, Columbus, Ohio

[21] Appl. No.: 904,129

[22] Filed: Sep. 5, 1986

[51] Int. Cl.$^4$ .................. C07D 487/14; C07D 491/22
[52] U.S. Cl. .................................. 544/225; 544/339; 544/343
[58] Field of Search .................. 544/339, 343, 225

[56] References Cited

U.S. PATENT DOCUMENTS 3,903,281  9/1975  Cox ...................................... 544/356

OTHER PUBLICATIONS

Griffin et al. Adv. Chem. Ser 142, 458 (1972).
Encylopedia Polymer Sci & Technology, vol. II, p. 268 (1969).
Buehler, Ed. "Survey, Organic Synthesis", vol. II (1978) p. 673.
Kanakarajan and Czarnik, J. Org Chem 51, 5241 (1986).
Kohne, Ann. Chem 1985, 522.
Rogers, J. Org. Chem 51, 3904.

*Primary Examiner*—Mark L. Berch
*Attorney, Agent, or Firm*—Sidney W. Millard

[57] ABSTRACT

Hexaazatriphenylene hexanitrile and various derivatives therefrom including its hexacarboxamide, hexacarboxylic acid and hexaacid salts and metal complexes, lower alkyl hexaesters of the hexacarboxylic acid, and hexacarboxylic trisanhydride are described along with their preparations initiating with reacting hexaketocyclohexane octahydrate with excess diaminomaleonitrile in acetic acid, preferably at reflux temperature, to provide the hexanitrile from which the other derivatives are prepared.

7 Claims, No Drawings

HEXAAZATRIPHENYLENE HEXANITRILE AND ITS DERIVATIVES AND THEIR PREPARATIONS

INTRODUCTION

This invention relates to hexaazatriphenylene hexanitrile (sometimes designated hexaazatriphenylenehexacarbonitrile) and related hexaazatriphylene compounds as well as their preparations and uses. More particularly, the invention concerns hexaazatriphenylene hexanitrile and related hexaazatriphenylene hexacarboxamide, hexacarboxylic acid and its salts and metal complexes, lower alkyl hexaesters of the hexacarboxylic acid, and hexacarboxylic acid trisanhydride compounds and like related compounds, and preparation processes for each proceeding from reacting hexaketocyclohexane octahydrate with excess diaminomaleonitrile and following with additional steps up to the isolation of the particular hexaazatriphenylene compound. Included in the invention for these compounds are uses for metal cation binding and metal value removal for various liquid media for metal recovery purposes and/or cleaning-up of the media purposes, and also other applications such as cross-linking agents in thermooxidatively stable polymer syntheses.

BACKGROUND OF THE INVENTION

Hexaazatriphenylene has been made previously, but one sequence is rather long and does not suggest any easy way to incorporate the kind of functionality present in hexaazatriphenylene hexanitrile (Nasielski-Hinkens. R.; Benedek-Vamos, M.; Maetens, D.; Nasielski, J.; *J. Organometal. Chem.*, (1981), 217, 179), while another was accomplished only in very low yield (Kohne, B.; Praefcke, K.; *Liebigs Ann. Chem.*, (1985), 522). Precursor materials for preparing the title compound are available commercially, but because of cost or other reasons one may want to prepare various starting materials, e.g. hexaketocyclohexane octahydrate, in-house as will be described later.

High-temperature resistant polymers are known materials with a wide range of present and future applications. Especially desirable for some applications are those polymers with high thermooxidative stability (i.e. they maintain structural integrity when heated to high temperatures in the presence of air or oxygen) and do not undergo significant loss of other physical properties. Illustrative of one such class are the phthalocyanine-type polymers (Keller, T.M.; Griffith, J. R.; *J. Flourine Chem.* (1979), 13, 315). Another such class of polymers are polyimides, and for high thermooxidative stability noticeably polyimide and like polymeric structures devoid of, or of low content, in their structures of hydrogen present as C-H bonds. Hexaazatriphenylene hexanitrile and its other hexaderivatives described herein offer potential for use, and are useful, for providing improved and new high thermooxidative stable polymers of several different chemical classes. This invention's compounds offer the advantage of compounds whose structure has a hexaazatriphenylene nucleus completely devoid of hydrogen while providing functional groups attached to the nucleus. For some of the invention's compounds, the attached functional groups, especially in the titled hexanitrile, advantageously are devoid completely of hydrogen. In other words, whatever hydrogen is present only is in their functional groups and is removed or removable during incorporation into the useful polymer. Various of the invention's compounds find utility in the preparation of high thermooxidative stable polymers as cross-linking agents or reactants, such as copolymerizing or co-condensation reactants, as additives, as constituents in various polymer formulations for binding metal fillers or for making the polymeric formulation more processable and/or machineable, and the like.

Various of the derivatives of hexaazatriphenylene hexanitrile should be useful as cross-linking agents in thermooxidatively stable polymer synthesis; the complete lack of hydrogens or of aliphatic carbons in, for example, hexaazatriphenylene trisanhydride should afford a resistance to thermal degradation in the presence of air. Co-polymers thusly prepared should bind metal ions owing to phenanthroline-like chelating sites; the potential to make cross-linked inorganic polymers also exists. The title compound itself and/or its monomeric derivatives will certainly be capable of multiple metal ion binding, and the use of a water soluble derivative such as hexaacid could well have intercalating and/or hydrolytic properties in biochemical systems.

With increasing needs to conserve valuable chemicals, including metals, by their isolation and recovery, and also increasing demands that chemical processing liquids, effluents, etc. be cleaned-up and significantly depleted of harmful constituents therein before their disposal, recycling or the like, a providing of new compounds for such applications is highly desirable. Some of the invention's compounds, noticeably the hexaacid, characterized by a structure nucleus of a hexaazatriphenylene moiety provide an unusual affinity for many cations and especially metal cations. This affinity also while not completely understood may be of the nature of chelation, covalent and/or ionic bonding, occlusion, or the like. Depending on the nature of the hexafunctional groups and particular liquids in which the various hexaazatriphenylene compounds are utilized, their specific functional groups can assist and increase the ability to tie-up or bind cations in the liquid. Generally, the metal ion/hexaazatriphenylene complex forms as a solid precipitate, which can be filtered out, or the liquid decanted from, and the cation value (e.g. metal) recovered from the isolated solid by chemical means (e.g. hydrolysis) or physical means (e.g. pyrolysis).

SUMMARY STATEMENT OF THE INVENTION

The invention concerns a hexaazatriphenylene compound of the structure

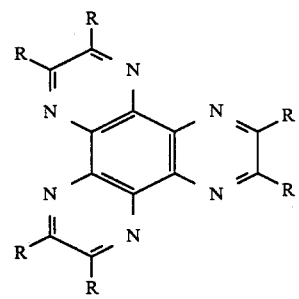

wherein each R individually is the same throughout and is selected from the group consisting of —C≡N, —CONH$_2$, —COOH, and —COOR' with R' being a lower alkyl radical of 5-carbon atoms or less, or wherein each of the three pairs of ring-adjacent R is —CO—O—CO—,. Especially preferred of these hexaazatriphenylene compounds is hexaazatriphenylene hexanitrile. Other preferred compounds are the hexaazatriphenylene hexacarboxylic acid, its lower alkyl ester and the trisanyhydride of the hexacarboxylic acid. Also included in the invention are hexaazatriphenylene derivatives prepared from hexaazatriphenylene hexanitrile. Of particular concern are the hexaazatriphenylene derivatives selected from the group of compounds consisting of hexaazatriphenylene hexacarboxamide, hexaazatriphenylene hexaacarboxylic acid and its metal salts and metal complexes, 5-carbon atoms or less alkyl hexaesters of hexaazatriphenylene hexacarboxylic acid, and hexaazatriphenylene hexacarboxylic acid trisanhydride.

The invention also concerns a process of preparing hexaazatriphenylene hexanitrile, which process comprises:

(a) reacting up to 0.03 molar hexaketocyclohexane octahydrate in acetic acid, containing less than 5% by volume of water, with diaminomaleonitrile, which is present in the acetic acid in a molar amount at least three times the molar amount of hexaketocyclohexane octahydrate, by heating to a temperature of at least about 100° C.; and (b) separating the hexaazatriphenylene hexanitrile from a resulting liquid reaction medium comprising said hexanitrile, remaining acetic acid, unused reactants and by-product. In this process the separating of solid hexaazatriphenylene hexanitrile should be while said resulting liquid reaction medium is at an elevated temperature above at least 100° C. to ensure purity of the produced and separated hexanitrile. Preferably, the process employs the diaminomaleonitrile in an amount of 1.5 to 4 times the theoretical amount to react completely the hexaketocyclohexane octahydrate. Preferably also, the process employs glacial acetic acid and heating to reflux temperature.

The invention also includes the process of preparing a hexaazatriphenylene derivative of hexaazatriphenylene hexanitrile, which derivative is selected from the group consisting of hexaazatriphenylene hexacarboxamide, hexaazatriphenylene hexacarboxylic acid and its alkali metal salts and metal complexes, 5-carbon atoms or less alkyl hexaesters of hexaazatriphenylene hexacarboxylic acid, and hexaazatriphenylene hexacarboxylic acid trisanhydride, with said process comprising:

(a) first, preparing the hexaazatriphenylene hexanitrile by (i) reacting up to about 0.03 molar hexaketocyclohexane octahydrate in acetic acid, containing less than 5% by volume of water, with diaminomaleonitrile, which is present in the acetic acid in an amount at least three times the molar amount of hexaketocyclohexane octahydrate, by heating to a temperature of at least about 100° C., and (ii) separating the hexaazatriphenylene hexanitrile from a resulting liquid reaction medium while said medium is at a temperature above at lest 100° C.; and (b) second, (i) for preparing the hexaazatriphenylene hexacarboxamide, dissolving said hexanitrile in concentrated sulfuric acid to provide a solution thereof and slowly adding the solution to ice water and following with separation of the hexacarboxamide therefrom, (ii) for preparing the hexaazatriphenylene hexacarboxylic acid, and its alkali metal salts, preparing a solution of said hexacarboxamide in trifluoroacetia acid, adding alkali metal nitrate in small portions totaling several molar times the amount of the hexacarboxamide in solution to the solution, pouring into ice water, collecting crude product by filtration, dissolving the crude product in aqueous sodium bicarbonate solution and filtering off any undissolved solid, and then adding alkali metal hydroxide solution to provide a precipitate of alkali metal haxaazatriphenylene hexacarboxylate which is separated, subsequently suspending and dissolving by heating the alkali metal hexaazatriphenylene hexacarboxylate in water and hydrolyzing the hexacarboxylate to provide the hexacarboxylic acid and separating the hexacarboxylic acid from its hydrolyzing medium;

(iii) for preparing the 5-crbon atoms or less alkyl hexaester of hexaatriphenylene hexacarboxylic acid, the mixing of the hexacarboxylic acid with greater than a theoretical amount of a 5-carbon atom or less alkanol and a small amount of acid and subsequently heating to provide a precipitate of the alkyl hexaester which is separated therefrom; and (iv) for preparing the hexaazatriphenylene hexacarboxylic acid trisanhydride, an adding of the hexaazatriphenylene hexacarboxylic acid to acetic anhydride and heating to about 115° C. under a nitrogen atmosphere, subsequently cooling and removing solvent under reduced pressure, following with recrystallization of the residue and with employing a small amount of dessicant, and then separating the trisanhydride from the recrystallization medium.

DETAILED DESCRIPTION OF THE INVENTION

For preparing the preferred compound, hexaazatriphenylene hexanitrile, of the invention one employs precursors of hexaketocyclohexane octahydrate and diaminomaleonitrile. While commercially available materials may be used, one may wish to prepare his own starting materials. For use in the illustrative examples, which follow later, hexaaketocyclohexane octahydrate was prepared in a two-step reaction from glyoxal; self-condensation to afford tetrahydroxyquinone proceeds as described previously (Fatiodi, A. J.; Sager, W. F.; *Org. Synth.*, Coll. Vol. V, p 1011), then oxidation to the desired octahydrate using a modification of literature method [a) Nietzki, R.; Benckiser, T.; *Berichte* (1885), 18 605; b) Ochiai, E.; Kobayaski, Y; Hagimura, T.; Takeuchi, S.; Fijimoto, M.; *Chem. Abstr.*, (1967), 66 104832]. There follows a description of one such preparation of hexaketocyclohexane octahydrate. The original procedure reported to Nietzki et al, supra, was modified as follows: Powered sodium tetrahydroxyquinone (10.8 g, 50 mmol) was added in portions to a stirred, ambient temperature solution of 25% $HNO_3$ (150 mL) over a period of ten minutes. The temperature of the vigorous reaction was controlled below 50° C. Colorless crystals formed and were collected by filtration, washed with cold water (3×30 mL), and dried to give the desired product (11.7 g, 80%): dec 95°–96° C. (lit. 95°–96° C.).

To prepare the preferred hexanitrile compound one reacts hexaketocyclohexane octahydrate with an excess of diaminomaleonitrile in refluxing glacial acetic acid to product hexaazatriphenylene hexanitrile in yields higher than 80%. This procedure has some analogy to that used by Skujins and Webb in their condensation of hexaketone with o-phenylenediamine (*Tetrahedron,* (1969), 25, 3935). The desired product is isolated by simple filtration from the hot reaction mixture and is analytically pure after drying. Its $^{13}$C NMR spectrum reveals the simple pattern expected for a compound with $D_{3h}$ symmetry, and one observes three singlets: one for nitrile carbons, one for peripheral aromatic carbons, and one for internal aromatic carbons. The compound is quite insoluble in most organic solvents, but solutions in DMF or DMOS (Dimethyl sulfoxide) can be made. A DMF (Dimethyl formamide) solution with tetrabutylammonium perchlorate as the supporting electrolyte was used to establish a chemically reversible coupled centered at −0.105 V ($\Delta E_p$ 100 mV) vs. aqueous SCE (−0.595 V vs. ferrocene) for hexaazatriphenylene hexanitrile leading to its radical anion; a second, irreversible couple leading to the dianion was observed at −0.495 V.

In the foregoing described preparation for high yield and product purity, it is important that acetic acid be used as the reaction medium, and preferably glacial acetic acid used. Water should be avoided in the reaction medium, as it not only leads to decreased yields, but its presence in large enough amounts may prevent the reaction from proceeding. For practical purposes, the acetic acid medium may contain up to about 5% by volume of water, if one can tolerate decreased yield of the desire hexanitrile along with probable contamination by by-product(s). The concentration and ratio of the two precursors to each other in the reaction medium is very important and probably crucial. A preferred and apparently optimum concentration for the hexaketocyclohexane octahydrate is an about 0.026 molar solution. Concentrations up to and including about 0.03 molar solutions are practical and useful, with greater concentrations leading to failure of the reaction to proceed and/or yields of impure product. Concentrations of 0.06 molar apparently are inoperative. The diaminomaleonitrile should be used in excess of the theoretical amount (i.e. three equivalents required for this reaction). For practical purposes a lower amount of diaminomaleonitrile of 1.5 to 4 times the theoretical amount appears necessary to assure a high yield of the hexanitrile product. A preferred amount is about 2.5 times the theoretical amount. Larger amounts may be employed, but are unnecessary and probably uneconomical. Of great importance is the temperature to carry forth the reaction. Generally, the reflux temperature (about 118° C.) of the acetic acid reaction medium is preferred and used and maintained by heating. Temperatures as low as 100° C. may be useful, but lower temperatures not only are impracticable, but little to no desired product apparently results. The reaction proceeds relatively rapidly with a practical reaction time of about ¼ to 2 hours preferred. Lower reaction times may provide lower yields. Reaction times beyond about 2 hours are unnecessary as no additional yield increases are noted. To recover a highly pure product, the formed product is removed (e.g. by filtering) from the acetic acid medium while it is hot, generally at about the same temperature (i.e. 100° C. to 118° C. reflux) at which the reaction is carried forth. Removal of desired hexanitrile at a lower temperature is accompanied by a by-product (probably the diacetate of diaminomaleonitrile) being removed in admixture therewith and an impure product yield.

While this process above has been described as operative in a batch-type manner, it will be apparent that the invention also contemplates and includes a continuous manner of process operation with continuous addition of materials and removal of product while maintaining operative process parameters.

While the invention contemplates inclusion of a number of derivatives, not explicitly named herein, of hexaazatriphenylene hexanitrile which will be obvious as well as methods of preparation from the teachings contained herein, the following describes the preferred derivatives and a process for preparation of each derivative, later illustrated by specific example.

Hydration of hexaazatriphenylene hexanitrile to hexaazatriphenylene hexaamide is accomplished readily using concentrated sulfuric acid at room temperature for 3 days. As in other reactions, involving derivatives of the hexanitrile, it is particularly important that all of the functional groups be converted to the next in very high yield; in that a procedure which affords the pentacarboxamidemononitrile as a contaminant, for example, would be of little to no use. $^{13}$C NMR of hexaazatriphenylene hexaamide reveals the sample pattern expected, except that the peripheral carbons are coupled to one of the amide NH's. It is not unexpected that the carbonyl carbon does not couple to the adjacent amide proton; an almost complete lack of carbonyl coupling to adjacent (but not directly bonded) protons allowed early $^{13}$C NMR investigators to observe signals before the advent of decoupling methods. Coupling to only one of the two amide NH's can be rationalized by recalling that $J_{C,H}$ experiences the same kind of angular dependence that $J_{H,H}$ does (Wiberg, K. B.; Lampon, G. M.; Cinla, R. P., Connor, D. S.; Schertler, P.; Lavanish, J.; Tetrahedron (1969), 21, 2749). The approximately 7 Hz coupling constant measured is consistent with long-range C—H coupling, and only the amide NH syn- to the carbonyl oxygen exists in a "w-conformation" with respect to the peripheral carbon; therefore, it is proposed that it is the only proton coupling to that carbon. Of special interest is the ability of laser desorption Fourier transform ion cyclotron resonance mass spectrometry (Marshall, A. G., "Fourier Transform Ion Cyclotron Mass Spectrometry", Acc Chem. Res. (1985), 18, 316), to yield a molecular ion for this highly polar, nonvolatile molecule (K+ complex ion observed). No other mass spectrometric technique tried gave any interpretable data on this compound.

Attempted basic hydrolyses (NaOH/H$_2$O/heat or Na$_2$O$_2$/H$_2$O) of hexaazatriphenylene hexaamide to the hexaacid derivative consistently yields mixture of partially-hydrolyzed polyacids, as determined by ion exchange chromatography and by paper electrophoresis. Acidic hydrolysis methods also give mixtures of insoluble products that are not readily characterized.

Success can be had in converting hexaazatriphenylene hexaamide to hexaazatriphenylene hexaacid under diazotizing conditions (Andenheim, H.; Bender, M. L.; *J. Am. Chem. Soc.* (1960), 82 1895) using sodium nitrite in trifluoroacetic acid. Precipitation of the sodium salt will afford the hexacarboxylate as confirmed by microanalysis and simple $^{13}$C NMR spectrum taken in D$_2$O/H$_2$O. As compared to the highly water-insoluble hexanitrile or hexaamide, the hexaacid derivative is very water soluble as is its polycarboxylate. Vigorous treatment with HCl will result in ion exchange and precipitation of a less soluble carboxylic acid form with no observable decarboxylation; acid-catalyzed esterification with methanol can yield the hexamethyl ester derivative in high yield.

Hexaazatriphenylene trisanhydride can be prepared by using hot acetic anhydride. This has some analogy to the known (Hirsch, S. S.; *J. Polym. Sci.* (1969), 7, 15) conversion of pyrazine-2,3,5,6-tetracarboxylic acid to its corresponding bisanhydride. Temperature control appears particularly important in preparing the trisanhydride derivative, as does starting with a sample of the hexaacid derivative that has been completely converted to the H+ form. Heating a suspension of the hexaacid derivative in freshly distilled acetic anhydride at 114°–116° C. for about 10 min yields a homogeneous solution that, upon evaporation, gives the trisanhydride derivative as a moisture-sensitive solid. Crystallization from acetonitrile/benzene/trifluoroacetic anhydride affords a crystalline solid, which can be characterized by $^{13}C$ NMR and IR (mass spectrometry and microanalysis in progress). Treatment of the $^{13}C$ NMR sample with one equivalent of $H_2O$ lead to a significantly complicated spectrum that, upon further addition of excess $H_2O$, again demonstrates a three line spectrum identical to that of the hexaacide derivative in the same solvent. The trisanhydride is much more soluble in organic solvents (e.g., acetonitrile) than the other prepared hexaazatriphenylene derivatives described above.

For the examples which follow: Melting points were taken on an Electrothermal melting point apparatus and are uncorrected; Microanalyses were made by a Canadian microanalytical service; Mass spectra were obtained by use of a Kratos-30 mass spectrometer; and FT-NMR spectra at 11.75 tesla (500 MHz) or 7.0 tesla (300 MHz) were obtained using Nicolet high-field NMR spectrometers.

EXAMPLE 1

Hexaazatriphenylene hexanitrile

A mixture of hexaketocyclohexane octahydrate (10.0 g, 32 mmol) and diaminomaleonitrile (26.0 g, 240 mmol) in glacial acetic acid (1200 mL) was heated to reflux with stirring for 2 h. The black reaction was filtered hot, and the solid was washed with hot glacial acetic acid (3×150 mL). Drying over KOH pellets at 150° C. and 0.01 torr for 2 h afforded a brown-black solid (10.1 g, 81%): mp 350° C.; $^{13}C$ NMR ($(CD_3)_2SO$) $\delta$114.2 (br s, CN's), 135.4 (s, internal Ar carbons), 141.6 (s, peripheral Ar carbons); IR (KBr pellet) 2250 cm$^{-1}$ (weak, CN). Desorption chemical ionization mass spectrum ($CH_4$): m/e 385 (100%, [M+1]+).

Anal. Calcd for $C_{18}N_{12}$: C, 56.25; H, O; N, 43.75. Found: C, 56.09; H, 0.14; N, 43.60.

EXAMPLE 2

Hexaazatriphenylene hexacarboxamide

A solution of hexaazatriphenylene hexanitrile (4.80 g, 12.5 mmol) in concentrated $H_2SO_4$ (100 mL) was stirred at room temperature for 72 h, then was added dropwise to rapidly stirred ice water (3 L). The solid was collected by filtration, washed with water (3×100 mL) and acetone (3×100 mL), and dried at 100° C. and 0.01 torr for 14 h to provide a grey-black solid (5.38 g, 87%): mp >350° C.; $^{13}C$ NMR (($CD_3)_2SO$) $\delta$140.5 (s, internal Ar carbons), 148.3 (d, J=7.3 Hz, coalesces to s with broad-band $^1H$ decoupling, peripheral Ar carbons), 166.2 (s, $CONH_2$s); IR (KBr pellet) 1680 cm$^{-1}$ (strong, C=O). Laser desorption FT ICR mass spectrum: m/e 531 (100%, [M+K]+).

Anal. Calcd for $C_{18}H_{12}N_{12}O_6 \cdot H_2O$: C, 42.35; H, 2.77; N, 32.94. Found: C, 42.62; H, 2.74; N, 33.00.

EXAMPLE 3

Hexaazatriphenylene hexacarboxylic acid

A solution of hexaazatriphenylene hexacarboxamide (4.92 g, 10 mmol; in trifluoroacetic acid (150 mL) was stirred at room temperature. Solid sodium nitrite (7.0 g, 90 mmol) was added to this solution portionwise over a period of 15 minutes, keeping the temperature under 25° C. by cooling with an ice bath. An initial brisk evolution of gas was noted and the black solution changed to an orange brown suspension. Acetic acid (150 mL) was added and the mixture was stirred for 12 h, poured into ice water (300 mL), and the crude product was collected by filtration. The solid was dissolved in sodium bicarbonate solution (20 g in 150 mL water) and filtered to remove any insoluble solid. The filtrate was treated with activated charcoal, heated to boiling, and filtered to give a clear yellow solution that was treated with a cold sodium hydroxide solution (20.0 g in 100 mL water). An immediate precipitation of sodium hexaazatriphenylene hexacarboxylate as a yellow solid occurred, and complete precipitation of the salt was effected by the addition of ethanol (30 mL). The product was filtered, washed with 50% aq. alcohol (3×50 mL), and dried under vacuum (100° C./0.1 torr) to afford 4.53 g of the polysodium salt of the hexaacid: IR (KBr pellet) $\mu$=1618 cm$^{-1}$ (C=O; $^{13}C$ NMR ($D_2O/H_2O$) $\delta$140.00 (s, internal carbons), 151.08 (s, peripheral carbons), 171.70 (s, carboxylate carbons).

The free acid was obtained as follows: Polysodium hexaazatriphenylene hexacarboxylate (2.54 g, 40 mmol) was suspended in water (100 mL), heated to 50° C., and acidified by adding concentrated HCl (100 mL). The mixture that formed was heated at 90° C. for one hour then was filtered, washed with 10% HCl (3×25 mL), and finally washed with deionized water (2×25 mL). The product was dried at 120° C./0.1 torr to give the hexacarboxylic acid (1.88 g, 89.5%) as its sesquihydrate: mp <350° C.; $^{13}C$ NMR ($D_2O$/dilute $NH_4OH$) $\delta$140.1 (s, internal Ar carbons), 151.2 (s, peripheral Ar carbons), 171.7 (s, carboxyl carbons); IR (KBr pellet) $\mu$=1730 cm$^{-1}$ (>C=O).

Anal. Calcd for $C_{18}H_6N_6O_{12} \cdot 1.5H_2O$: C, 41.16; H, 1.73; N, 15.99. Found: C, 41.07; H, 1.91; N, 15.82.

EXAMPLE 4

Hexamethyl ester of hexaazatriphenylene hexacarboxylic acid

A solution of hexaazatriphenylene hexacarboxylic acid (525 mg of the sesquihydrate, 1 mmol) in absolute methanol (200 ml) and concentrated sulfuric acid (1 ml) was heated to reflux with stirring for 10 h. The solid was collected by filtration, washed with aqueous methanol (50 ml) and dried at 100° C. and 0.01 torr for 6 h to provide a cream colored solid (490 mg; 84%) that could be recrystallized from acetonitrile: mp <350° C.; $^{13}C$ NMR (DMSO-$d_6$) $\delta$164.02 (s, ester carbonyl carbons), 145.08 (s, internal or peripheral Ar carbons), 142.23 (s, internal or peripheral Ar carbons), 53.63 (s, methyl carbons); $^1H$ NMR ($CDCl_3/CF_3COOH$) $\delta$4.17 (s, $CH_3$); IR (KBr pellet) $\mu$=1750 cm$^{-1}$ (strong, C=O). FAB mass spectrum: m/e 583 (M+1).

Anal. Calcd for $C_{24}H_{18}N_6O_{12}$: C, 49.48; H, 3.09; N, 14.43.

Found: C, 49.12; H, 3.14; N, 14.50.

EXAMPLE 5

Hexaazatriphenylene hexacarboxylic acid trisanhydride

Hexaazatriphenylene hexacarboxylic acid (1.25 g, 23.8 mmol) was added to freshly distilled acetic anhydride (60 mL) and heated to 115°±2° C. under a nitrogen atmosphere. The vigorously stirred mixture turned to a clear brown solution within ten minutes, then heating was discontinued and the solution was allowed to cool over a period of 20 minutes. The solvent was removed by rotary evaporation under reduced pressure and the residue was recrystallized from acetonitrile and benzene (using a few drops of trifluoroacetic acid as desiccant) to give the trisanhydride (963 mg, 95%) as moisture-sensitive needles: mp >350° C.; $^{13}$C NMR (CD$_3$CN) δ159.58 (s, carbonyl carbons), 148.62 (s, internal or peripheral Ar carbons), 148.15 (s, internal or peripheral Ar carbons); IR (KBr pellet) $\mu$=1820 (strong), 1880 cm$^{-1}$ (<C=O).

To illustrate applications of a hexaazatriphenylene compound for a cation, especially metals, recovery purposes a stock solution of $1\times 10^{-3}$ molar solution of the hexacid derivative in water was prepared. Other stock solutions of about $10^{-2}$ moles in water were prepared for each of the following cations $Pb^{2+}$, $Cd^{2+}$, $Hg^+$, $Hg^{2+}$, $Fe^{3+}$, $Cu^{2+}$, $Ca^{2+}$, $Sr^{2+}$, $Ag^+$, $Zn^{2+}$, $Mn^{2+}$, $UO_2^{2+}$, $Ni^{2+}$, $Fe^{2+}$ and $Cr^{3+}$. When about 10 ml of aliquots of the aqueous hexaacid derivative were admixed with about 10 ml of each of the cation solutions, an insoluble precipitate was formed and/or color change occurred. Of those in which a distinctive color change was observed; for $Pb^{2+}$ with $Pb(ClO_4)_2$ in solution, a yellow precipitate was noted; $Fe^{2+}$ solution provided a bright blue or dark green color and no visible precipitate; $Cd^{2+}$ gave a bright yellow color and within a few seconds gave a yellow precipitate; $Sr^{2+}$ with $Sr(ClO_4)_2$ in solution provided a colorless precipitate; $Hg^{2+}$ with $Hg(ClO_4)_2$ in solution gave a red precipitate; $Hg^+$ from $Hg(ClO_4)$ in solution gave a brown precipitate, $UO_2^{2+}$ from $(UO_2)(ClO_4)_2\cdot 6H_2O$ in solution gave a bright yellow color; $Fe^{3+}$ in solution, provided yellow precipitate; $Cu(ClO_4)_2$ gave a turbidity upon admixing; $Ca^{2+}$ from $Ca(ClO_4)_2$ in solution gave a light yellow color precipitate; and $Ag^+$ from $AgNO_3$ in solution gave a bright yellow precipitate. In each instance where a precipitate formed, it is feasible, such as by filtration to separate the precipitate from the admixture and thus provide a water having a significantly decreased metal cation content.

As described above for hexaazatriphenylene hexacarboxylic acid, one also by like technique may recover or remove various cations from various liquid media, especially water solutions containing metal cations, by employing in place of the hexaacid any of hexaazatriphenylene hexacarboxylic acid trisanhydride, metal salts, e.g. sodium, or the like salts, and metal complexes of the hexaacid, or 5-carbon atoms or less alkyl hexaesters of the hexaazatriphenylene hexacarboxylic acid.

Additionally as described above and by like technique hexaazatriphenylene hexanitrile may be used to remove $Cu^+$ from solution in DMSO in that an adding of the hexanitrile in CuCl and CuI solutions in DMSO caused precipitates to form, which precipitates are removable and collectible by conventional techniques, such as decanting and filtration.

J. R. Griffith et al. have prepared phthalonitrile resins through heating of a melt of a phthalonitrile containing a suspension of clean copper flake (Griffith, J. R.; O'-Rear, J. G.; Walton, T. R.; "Phthalonitrile Resins"; Adv. Chem. Ser. (1972), 172, Ch. 39, p 458-464). Hexaazatriphenylene hexanitrile is a useful additive for such phthalonitrile resins and upon inclusion therein serves as a cross-linker and filler. For example, the Griffith et al (supra) page 461 polymerization procedure may be modified with their employed phthalonitrile being a mix comprising about 95% by weight of Griffith's phthalonitrile and about 5% by weight of hexaazatriphenylene hexanitrile. The hexanitrile dissolves in the melt of the phthalonitrile and crosslinks the resulting prepared phthalocyanine polymer, which has useful properties and is a useful polymeric material.

Useful polyimide copolymers from hexaazatriphenylene hexacarboxylic acid trisanhydride are contemplated through reaction of it with known diamines, such as ethylene diamine or the like. Useful copolymers from hexaazatriphenylene hexacarboxamide are contemplated through reaction of it with various known organic dihalides, such as α,α',-dichloro-p-xylene and the like.

It will be appreciated that changes and modifications may be made in the foregoing described embodiments of the invention without departing from the true scope of the invention. Accordingly, the preceding disclosure is to be construed as illustrative and not limiting with the scope of the invention defined solely by the claims, which follow.

We claim:

1. A hexaazatriphenylene compound of the structure

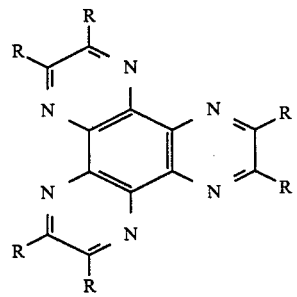

wherein each R individually is the same throughout and is selected from the group of —C≡N, —CONH$_2$, —COOH, and —COOR' with R' being a lower alkyl radical of 5-carbon atoms or less, or wherein each of the three pairs of ring-adjacent R is —CO—O—CO—.

2. The hexaazatriphenylene compound of claim 1 which is hexaazatriphenylene hexanitrile.

3. The hexaazatriphenylene compound of claim 1 which is the hexacarboxylic acid, or the lower alkyl ester thereof or the trisanhydride thereof.

4. A metal salt or metal complex of the hexaacid hexaazatriphenylene derivative from hexaazatriphenylene hexaniltrile in which each of its six —C≡N nitrile functional groups are replaced respectively each by a —COOH functional group.

5. The hexaazatriphenylene compound of claim 1 which is hexaazatriphenylene hexacarboxamide.

6. The hexaazatriphenylene compound of claim 1 which is hexaazatriphenylene hexacarboxylic acid trisanhydride.

7. The hexaazatriphenylene compound of claim 1 which is hexaazatriphenylene hexacarboxylic acid or 5-carbon atoms or less alkyl hexaesters of hexaazatriphenylene hexacarboxylic acid.

* * * * *